United States Patent
Guler et al.

(10) Patent No.: US 11,849,923 B2
(45) Date of Patent: Dec. 26, 2023

(54) WEARABLE BLOOD GAS MONITOR

(71) Applicants: Ulkuhan Guler, Shrewsbury, MA (US);
Ian Costanzo, Worcester, MA (US);
Devdip Sen, Worcester, MA (US);
Lawrence Rhein, Worcester, MA (US)

(72) Inventors: Ulkuhan Guler, Shrewsbury, MA (US);
Ian Costanzo, Worcester, MA (US);
Devdip Sen, Worcester, MA (US);
Lawrence Rhein, Worcester, MA (US)

(73) Assignee: Worcester Polytechnic Institute, Worcester, MA (US)

(*) Notice: Subject to any disclaimer, the term of this patent is extended or adjusted under 35 U.S.C. 154(b) by 311 days.

(21) Appl. No.: 17/066,570

(22) Filed: Oct. 9, 2020

(65) Prior Publication Data
US 2021/0106316 A1    Apr. 15, 2021

Related U.S. Application Data

(60) Provisional application No. 62/913,299, filed on Oct. 10, 2019.

(51) Int. Cl.
*A61B 10/00* (2006.01)
*A61B 5/145* (2006.01)
*A61B 5/00* (2006.01)

(52) U.S. Cl.
CPC .......... *A61B 10/00* (2013.01); *A61B 5/14542* (2013.01); *A61B 5/443* (2013.01); *A61B 5/6832* (2013.01); *A61B 2010/0083* (2013.01)

(58) Field of Classification Search
CPC ..... A61B 10/00; A61B 5/14542; A61B 5/443; A61B 5/6832; A61B 2010/0083;
(Continued)

(56) References Cited

U.S. PATENT DOCUMENTS 6,325,978 B1    12/2001  Labuda et al.
2007/0172392 A1*  7/2007  Sen ............... A61B 5/14556
                                              422/82.08
(Continued)

OTHER PUBLICATIONS

M. Y. Berezin, et al., "Fluorescence Lifetime Measurements and Biological Imaging," Chem. Rev., vol. 110, No. 5, pay 2010, pp. 1-128, Department of Radiology, Washington University School of Medicine.
(Continued)

*Primary Examiner* — Eric F Winakur
*Assistant Examiner* — Abid A Mustansir
(74) *Attorney, Agent, or Firm* — Armis IP Law, LLC (57) ABSTRACT

A transdermal oxygen patch measures an oxygen concentration based on transcutaneous oxygen diffusing through an epidermal surface of a patient. Transcutaneous oxygen differs from hemoglobin-bound oxygen often measured in a patient blood flow. The patch employs an indicator responsive to an oxygen presence for emitting light having an intensity and lifetime (duration) based on the oxygen presence. An optical receptor is in communication with logic for receiving the intensity of emitted light and computing the oxygen concentration based on the received intensity and lifetime (duration). A wireless transmitter conveys the results to a base station or monitoring counterpart for untethered patient monitoring. Low power demands and circuit footprint are amenable to a wearable device such as a patch for continuous use.

10 Claims, 11 Drawing Sheets

(58) Field of Classification Search
CPC .......... A61B 5/0002; A61B 2562/0233; A61B 5/14552; A61B 5/6823; A61B 5/6833; A61B 5/7225; A61B 2503/045; G01N 2021/6432; G01N 2021/7786; G01N 21/6428; G01N 21/77
See application file for complete search history.

(56) References Cited

U.S. PATENT DOCUMENTS

| | | |
|---|---|---|
| 2010/0292549 A1 | 11/2010 | Shuler |
| 2016/0159842 A1* | 6/2016 | Evans ................ A61B 5/14552 540/465 |
| 2019/0021672 A1 | 1/2019 | Bremer |
| 2019/0150811 A1 | 5/2019 | Evans et al. |

OTHER PUBLICATIONS

M. Y. Berezin, et al., "Fluorescence Lifetime Measurements and Biological Imaging," Chem. Rev., vol. 110, No. 5, pay 2010, pp. 2641-2684, Department of Radiology, Washington University School of Medicine.

International Search Report, PCT/US2020/054900, dated Jan. 21, 2021, pp. 1-7.

* cited by examiner

WEARABLE BLOOD GAS MONITOR

RELATED APPLICATIONS

This patent application claims the benefit under 35 U.S.C. § 119(e) of U.S. Provisional Patent App. No. 62/913,299, filed Oct. 10, 2019, entitled "WEARABLE BLOOD GAS MONITOR," incorporated herein by reference in entirety.

BACKGROUND

Blood gas testing is an effective tool for analysis and diagnosis of many human physiological parameters. Blood chemistry can be an effective indicator of many bodily functions and conditions. Among the vital signs of human body, respiration is a key component of a person's health. Respiratory health can be quantified by rate, volume, and blood-gas content. Traditional respiration monitoring methods such as arterial blood gas monitoring and pulse oximetry have certain advantages and disadvantages.

SUMMARY

A transdermal oxygen patch measures an oxygen concentration based on transcutaneous oxygen diffusing through an epidermal surface of a patient. Transcutaneous oxygen differs from a measurement of saturated oxygen often measured in a patient blood flow. The patch employs an indicator responsive to an oxygen presence for emitting light having an intensity and lifetime based on the oxygen presence. An optical receptor is in communication with logic for receiving the intensity and lifetime (i.e. duration) of emitted light and computing the oxygen concentration based on the received intensity and lifetime. Low power demands and circuit footprint are amenable to a wearable device such as a patch for continuous use.

Configurations herein are based, in part, on the observation that oxygen sensing is frequently employed in many physiologic contexts due to its prevalent nature in essential human respiration. Oxygen in various forms and concentrations is found abundantly throughout living tissue, and therefore is often a reliable indicator of proper and healthy physiology. Unfortunately, conventional approaches to oxygen monitoring rely on oxygen saturation in blood, relating to hemoglobin-bound oxygen (oxyhemoglobin) in oxygenated blood. Measurement of oxygen concentration in tissue conventionally requires a robust apparatus with heating and power requirements inconsistent with a portable device. Oxygen concentration measures the oxygen concentration based on partial pressure of oxygen dissolved in the bloodstream, and is often preferred to a measurement of oxygen saturation, or may be taken in conjunction with saturated $O_2$.

Accordingly, configurations herein substantially overcome the shortcomings of conventional, bulky oxygen detection by providing a wearable oxygen sensor in the form of a patch or epidermal appliance for measuring transcutaneous oxygen upon diffusion through the epidermal surface. A photoluminescent indicator emits light responsive to an illuminating stimuli in a manner that varies with the presence of the diffused oxygen. An electronic circuit performs computations and implements logic for determining the oxygen concentration of the underlying tissue based on the partial pressure of the oxygen computed by the system.

In further detail, configurations below disclose a system and method implemented by a blood gas measurement device, including an optical source operable for emitting light, a sensing film adapted for adherence to an epidermal surface and responsive to gaseous diffusion from the epidermal surface. The sensing film has a luminophore responsive to emit light responsive to the optical source, such that the emitted light is based on a gaseous diffusion through the light sensitive medium. A photodetector sensitive to re-emitted light from the sensing film is coupled to an electronic circuit having logic responsive to a signal from the photodetector for computing a level of a blood gas based on the re-emitted light. A wireless transmitter completes the wearable device for monitoring patient oxygen concentration in a form factor suitable for implementation as a small patch or similar untethered personal device.

In a particular configuration directed to oxygen in the blood, the optical source emits light in a blue spectrum, and the photodetector is sensitive to light in a red spectrum. The sensing film may be a luminescent sensing film adapted for adherence to an epidermal surface. In one configuration, the luminescence of the fluorophore functional groups is quenched in the presence of oxygen, reducing the intensity and lifetime of the re-emitted red light. Change in the intensity and lifetime of the re-emitted red light received by the photodetector is inversely proportional to the change in the concentration of oxygen based on the partial pressure of transcutaneous oxygen ($PtcO_2$) diffusing from the epidermal surface. The wavelength sensitivity is specific to particular luminophores in the luminescent sensing film, as is the remitted light. Alternative sensing films may involve different wavelengths. For example, a rubidium based sensing film is responsive to a greener color light and remits a more orange wavelength. Various sensing films may be employed, and the optical sources and photodetectors matched to the wavelength sensitivity for producing a response to oxygen. Still further, a sensitivity to other gases may also be employed.

In contrast to conventional approaches, the $PtcO_2$ sensor and associated logic is encapsulated in a wearable patch or low-profile, adhesive arrangement and includes a wireless transmitter for offloading storage and analytics capability. While conventional $SpO_2$ measurement has been achieved in finger-attached wired sensors, compact sensing of $PtcO_2$ oxygen levels has typically required a larger footprint device including a heating element for electrochemical sensing of perfusion. Therefore, conventional approaches employ an electrochemical, rather than optical measurement medium and are not feasible for miniaturization due to the power demands of the heating element.

Those skilled in the art should readily appreciate that the programs and methods defined herein are deliverable to a user processing and rendering device in many forms, including but not limited to a) information permanently stored on non-writeable storage media such as ROM devices, b) information alterably stored on writeable non-transitory storage media such as solid state drives (SSDs) and media, flash drives, floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions, including virtual machines and hypervisor controlled execution environments. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The description below presents an example of a wearable device for measurement of oxygen ($O_2$) by transcutaneous partial pressure ($PtcO_2$), which differs from conventional measurement because conventional approaches measure saturated oxygen ($SpO_2$). Saturated oxygen is bound to hemoglobin, while $PtcO_2$ measurement refers to a concentration of total oxygen. Depending on the medical context, $PtcO_2$ based readings have an advantage over conventional $SpO_2$, either alone or in conjunction with $SpO_2$ readings.

A blood gas measurement device includes an optical source and a sensing film adapted for adherence to an epidermal surface and responsive to gaseous diffusion from the epidermal surface. The sensing film is sensitive to the gas or gases targeted for sensing based on re-emittance properties that are affected by transdermal gaseous diffusion. An optical source, typically an LED for low power and heat properties, emits a light directed to the sensing film. A photodetector is sensitive to re-emitted light from the sensing film based on the optical source, and logic responsive to a signal from the photodetector computes a level of a blood gas based on the re-emitted light.

Photoluminescence refers to the emission of photons produced in certain molecules during de-excitation and is one of the possible physical effects resulting from the interaction between light and matter. When a luminescent molecule absorbs a photon, it is excited from a ground state to some higher vibrational level, and emits light upon its return to the lower state. The subsequent de-excitation processes are depicted below in FIGS. 4 and 5.

In the presence of molecular oxygen, the photoluminescence of such molecules is quenched via a radiationless deactivation process which involves molecular interaction between the quencher and the luminophore (collisional quenching) and it is therefore diffusion limited. The mechanism by which oxygen quenches luminescence is not germane to the disclosed approach, however it has been suggested that the paramagnetic oxygen causes the luminophore to undergo intersystem crossing to the triplet state while molecular oxygen goes to the excited state) and then returns to ground state.

Figure 1:
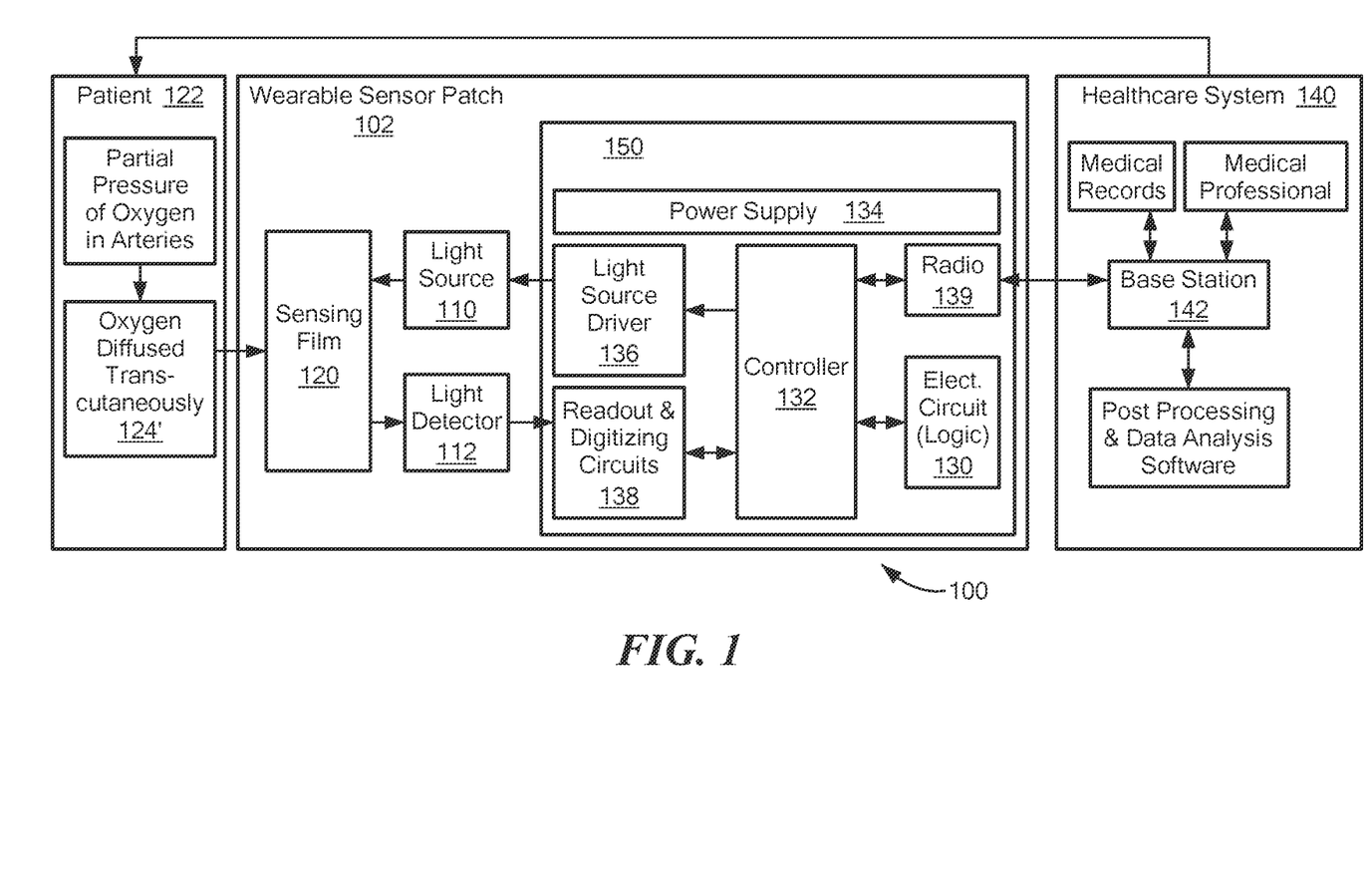
FIG. 1 is a system context diagram including a wearable sensor patch suitable for use with configurations herein.

FIG. 1 is a system context diagram including a wearable sensor patch suitable for use with configurations herein. Referring to FIG. 1, a blood gas measurement device 100 includes an optical source 110 and a light sensitive medium 120 such as a sensing film. The light sensitive medium 120 is configured to emit light responsive to the optical source 110, in which the emitted light is based on a gaseous diffusion through the light sensitive medium 120. A photoreceptor 112 is disposed for receiving the emitted light, and logic 130 coupled to the receptor 112 computes a quantity of the gaseous diffusion based on the emitted light.

In an example configuration, the device 100 takes the form of a wearable patch 102 adhered to or adjacent to the skin (epidermal surface) of a patient 122 for disposing a sensing circuit 150 thereon. An electronic circuit and/or processor instruction sequence implements the logic 130 which computes the oxygen concentration based on the duration and intensity of the emitted light. The photoreceptor 112 receives the light, and readout and digitizing circuits 138 transform and digitize the received light into intensity and lifetime (duration) values employed by the logic 130. A controller 132 is driven by a power supply 134 for powering the readout and digitizing electronics 138, controller 132, radio 139 and a light source driver 136 activating the LED light source 110. The controller 132 couples to the readout and digitizing circuit 138 for receiving emitted light. A radio 139 wirelessly couples to a base station 142 for gathering and transporting the computed oxygen levels, and may take the form of a personal device, hospital monitor, data logger or any suitable network device for capturing the computed oxygen levels and related data without encumbering the patient 122 with bulky devices. The patient data may then be recorded, stored and analyzed according to the patient's healthcare regimen. In contrast to conventional tethered approaches which require an electronic connection (wire), the radio 139 implements a wireless connection to a monitoring base station 142 for receiving and coalescing patient data and generating needed alerts and reports resulting from the oxygen concentration.

Figure 2:
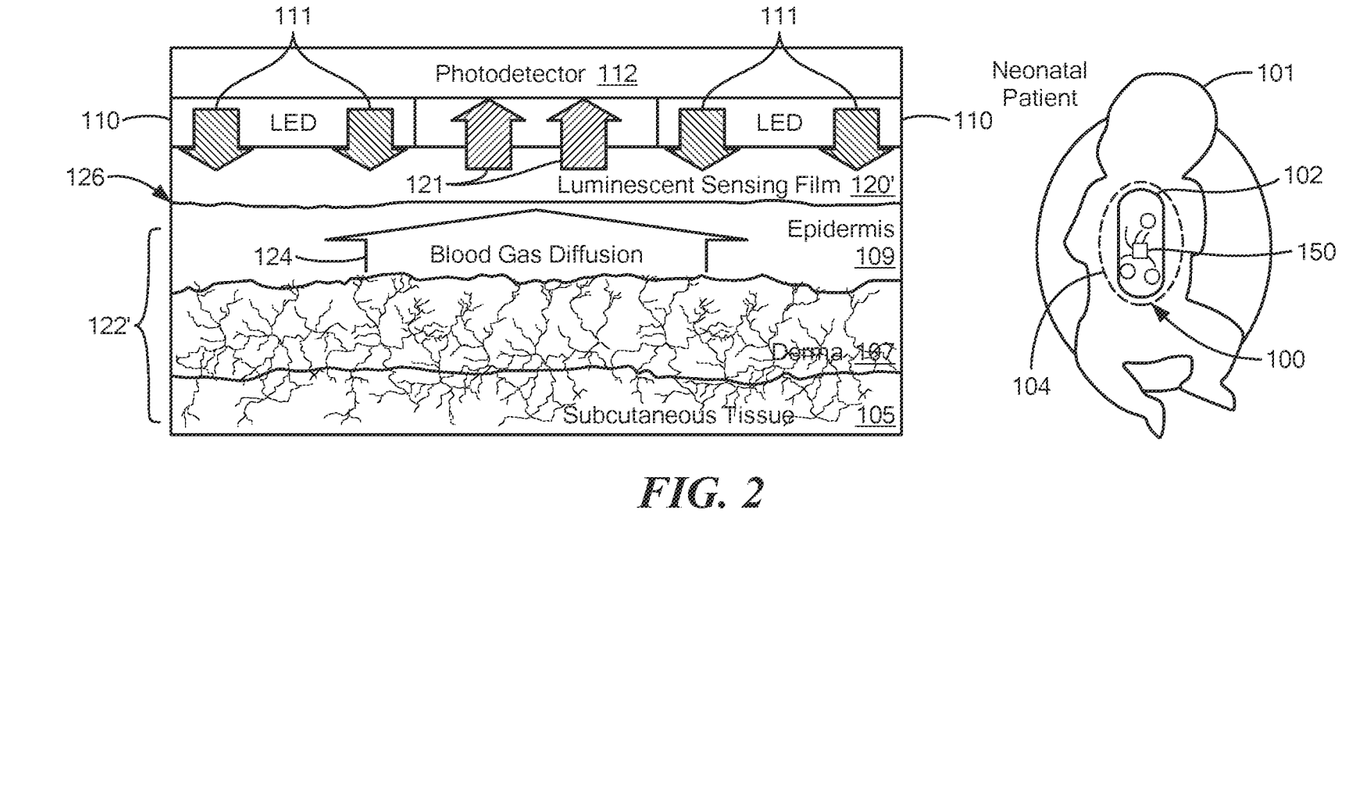
FIG. 2 shows a side cutaway view of the wearable patch of FIG. 1 in communication with an epidermal surface of a patient.

FIG. 2 shows a side cutaway view of the wearable patch 102 of FIG. 1 adhered to an epidermal portion 104 in communication with an epidermal surface 126 of the patient 122. Referring to FIGS. 1 and 2, the light sensitive medium 120 takes the form of a luminescent sensing film 120' adapted for communication with a gaseous diffusion source for receiving the gaseous diffusion. Diffused gases 124 including oxygen diffuses through dermal layers 122' of the patient 122 and through the sensing film 120. Subcutaneous tissue 105, derma 107 and epidermis 109 define the dermal layers 122' that are the source of the transcutaneously diffused oxygen 124'. The sensing film 120 is maintained in communication with the epidermal surface 126 by a collection medium adapted to engage a surface for coupling the light sensitive medium to a source of the gaseous diffusion. The collection medium may take the form of an adhesive, taped, or strapped patch for directing the diffused gases 124 from the surface to the collection medium.

For example, in a particular use case, collection medium is a planar epidermal patch 102 adapted for receiving gaseous diffusion from an infant 101 patient. The ability to remotely monitor infants could improve the feasibility of early discharge and reduce the risk of undiagnosed issues becoming significant after hospital release. Continuous and accurate remote tracking of vital respiratory parameters in a fully wireless manner could provide relevant and accurate data to the caregiver to inform the course of treatment. Configurations herein address the need to monitor patience's transcutaneous oxygen level remotely and safely by a medical professional with a light and low-height profile wearable device. Conventional vital monitoring systems, especially those that monitor blood gas status are typically large, bulky bed-side machines with wired electrodes and are usually used in a hospital setting. These machines require the patient to be tethered to a hospital bed with limited mobility.

Dermal placement of the patch 102 can be made elsewhere such as the abdomen or torso where it is less susceptible to patient movement, further enhanced by the omission of wired tethers. Such a patch encloses the light sensitive medium 120 in a sealing engagement with the dermal surface 126 for quantifying the transdermal oxygen emitted or diffused through the patch.

It its most basic form, the patch 102 and sensing device 100 perform a method for sensing an oxygen concentration based on transcutaneous oxygen 124' by receiving a diffusion of oxygen 124' and other gases 124 through the transcutaneous surface 126. The patch 102 adheres the light sensitive medium 120 to the transcutaneous surface 126, such that the light sensitive medium 120 has a photoluminescent response to the diffused oxygen 124'. A pulsed light 111 from the light source 110 on the light sensitive medium 120 causes the photodetector 112 to receive an emitted light 121 in response to the diffused oxygen. The logic 130 computes the partial pressure of oxygen value based on an oxygen sensitive luminophore in the light sensitive medium 120 responsive to quenching of the emitted light 121 inversely with the oxygen presence. In other words, the emitted light "fades" faster with greater oxygen, now discussed in more detail below.

Figure 3:
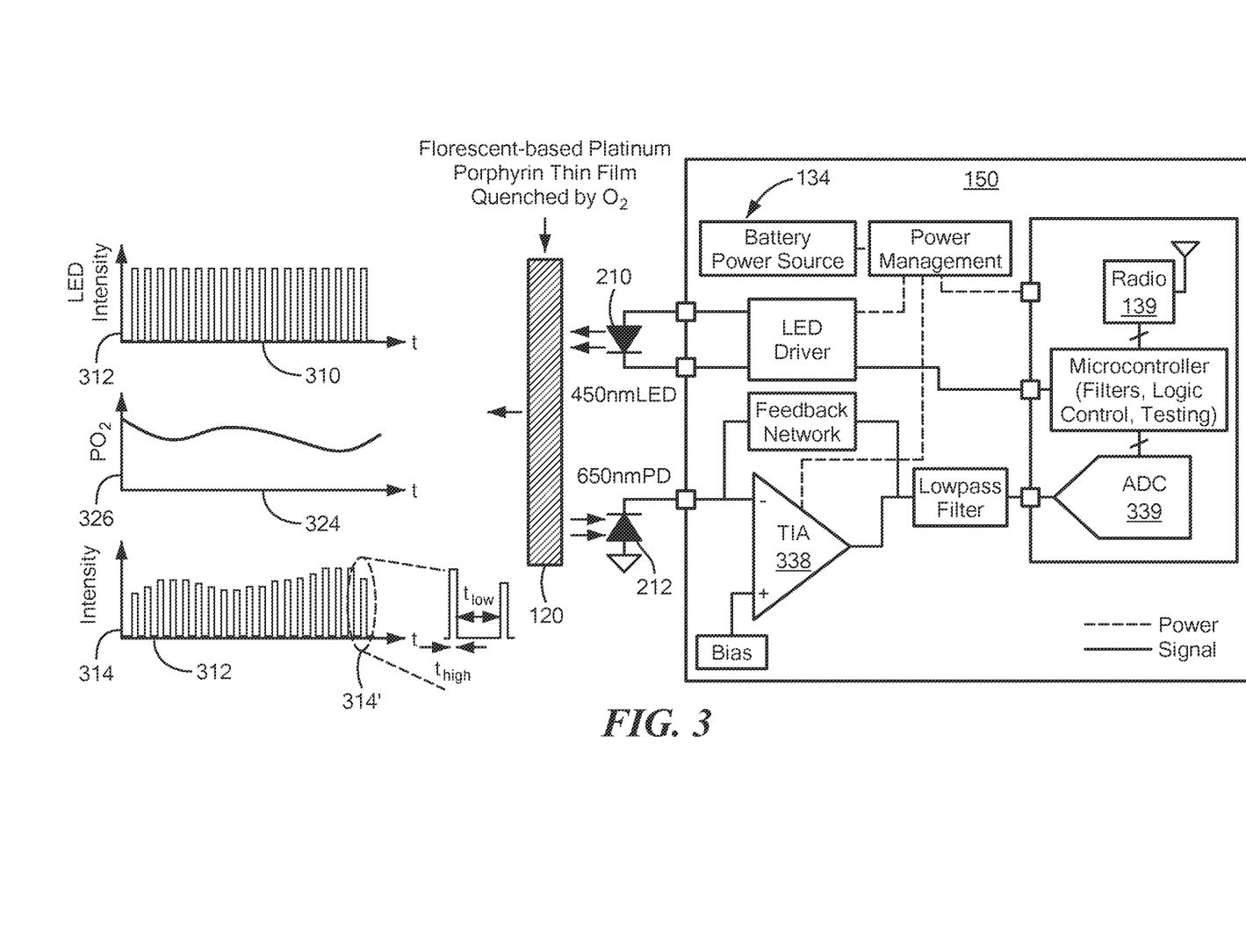
FIG. 3 shows a schematic view of a light intensity and processing circuit for the wearable patch of FIG. 2.

FIG. 3 shows a schematic view of a light intensity and processing circuit for the wearable patch of FIG. 2. Referring to FIGS. 1-3, as described above, the light sensitive medium 120 is a sensing film adapted for adherence to an epidermal surface 126 and responsive to gaseous diffusion from the epidermal surface. In FIG. 3, the device 100 is shown in a schematic of the fluorescent-based transcutaneous oxygen sensing system. A low power transimpedance amplifier and low power microcontroller connect to wireless system and powered by a coin cell battery. Alternate configurations may employ any suitable power arrangement, such as a coin cell, thin film battery, wireless power link, or similar methods. The disclosed system communicates to a base station 142 using a wireless protocol, such as Bluetooth®, Bluetooth LE, ZigBee®, WiFi, NFC (Near Field Communication) or similar approach consistent with FDA (Food and Drug Administration) and other governmental recommendations or guidelines for health related devices.

In the example of FIG. 3, the light source 110 is provided by a blue LED 210 having a wavelength around 450 nm. The LED 210 emits a pulsed intensity shown by graph 310 in a series of fixed intensity bursts or flashes. The light sensitive medium 120 is a thin film of platinum porphyrin (Pt-porphyrin) or other luminescent material such as rubidium, and emits (or remits) a red light in a wavelength around 650 nm received by a red light photodetector 212. The gaseous oxygen diffused 124' during the blue light emission is shown in graph 324. It can be observed that an intensity 314 of the emitted red light varies inversely with the partial pressure ($PO_2$) 326 of diffused oxygen, responsive to constant intensity 312 pulses of blue light. The remitted red light varies based on a quenching effect of oxygen on an excitation of a luminophore in the light sensing medium 120, thus reducing the red light response as oxygen increases, as shown in dotted line region 314' as the time t[high] transitions to t[low] in the presence of oxygen, described in further detail below. The luminescent material has the property of remitting light having an intensity and duration quenched by the presence of oxygen, therefore allowing oxygen measurement by observing the intensity and lifetime of the remitted light. The intensity/lifetime value of the remitted red light is received by a transimpedance amplifier 338 and converted by an analog/digital converter 339 for processing by logic 130. The intensity and lifetime are related as discussed below with respect to FIG. 9; in general, a lower oxygen presence mitigates the quenching effect and results in a greater intensity and lifetime of the remitted light. Measurement based on lifetime (duration) of the return pulses tends to be more resistant to factors such as LED fading/age and skin color variations.

Figure 4:
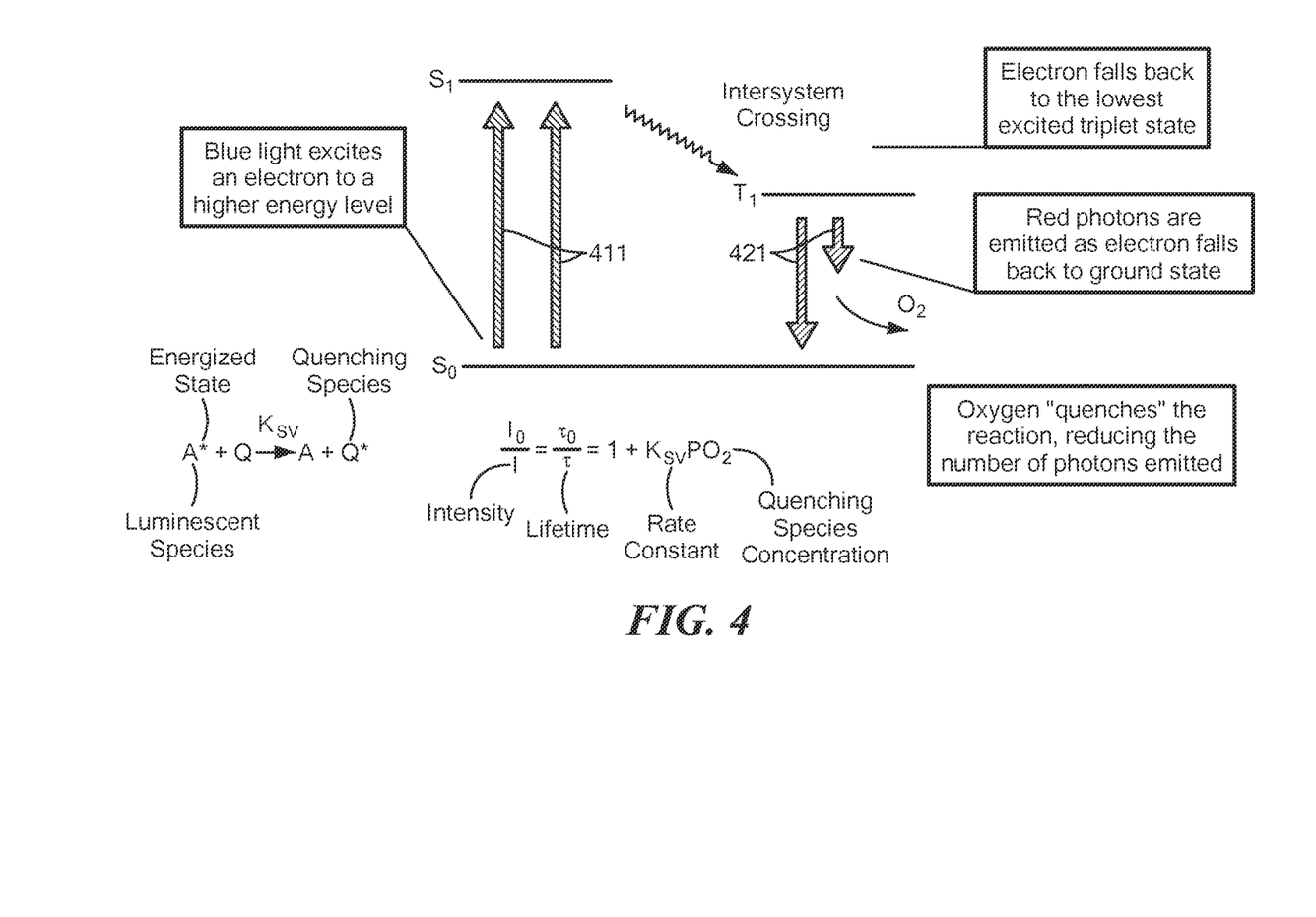
FIG. 4 is a diagram of light emission energy received by the circuit of FIG. 3.

FIG. 4 is a diagram of light emission energy received by the circuit of FIG. 3. Referring to FIGS. 2-4, in the excitation response of 314', a quenching effect of oxygen on the photoluminescent sensing film 120' is shown. The light sensitive medium 120 has a photoluminescent response and an oxygen based decay responsive the diffusion source for emitting a red light 121 inversely proportional with a partial pressure of oxygen in the gaseous diffusion 124. The sensing film 120' includes an oxygen sensitive luminophore for exhibiting an emission of red light 121 in response to the blue light 111 based on a partial pressure of oxygen diffused through the light sensitive medium 120.

Benefits of the claimed approach will be apparent with reference to conventional approaches. Traditional devices measure $PtcO_2$ electrochemically, using methods requiring a heating element that increases the diffusion of $O_2$ from blood vessels, thus increasing the concentration of $O_2$ in the gas 124 above the targeted skin area. However, a heating element negatively affects the feasibility of a miniaturized $PtcO_2$ wearable as it substantially increases the wearable device size and the power requirement. In addition, the hotspot irritates and may even burn the skin during continuous monitoring.

To overcome such limitations, the disclosed approach employs a fluorescence-based method that allows the use of comfortable dry electrodes without the need for heating. This method uses a thin film consisting of platinum porphyrin (Pt-porphyrin) or similar luminophore based medium. When a luminescent molecule absorbs a photon, it becomes excited from its ground state (S0) to some higher vibrational level of either the first or second electronic state (S1 or S2). When the film 120' is exposed to blue light 411, it emits red light 421, the intensity and lifetime of which are inversely proportional to the concentration of $O_2$ 124 around the film as the energy level reaches S1 and following the excitation by the pulse of blue light, fall back to an energy level shown by S0. The fluorescence of the thin film is typically measured in terms of its lifetime (i.e. fall time) where t0 is the lifetime of the film fluorescence without the quencher (oxygen), and t is the lifetime of the fluorescence with the quencher. Conventional approaches refer to the so-called Stern-Volmer relationship in reference to the kinematics of quenching, discussed further below in FIG. 9.

The disclosed example includes a wearable or adhesive patch having the luminescent film through which patient-diffused oxygen passes. An oxygen presence passing through or adjacent the luminescent material causes the oxygen sensitive quenching response from the optical source. Various arrangements of luminescent materials in conjunction with the patient may be employed, along with corresponding photoreceptors and optical sources with light wavelengths (colors) based on the luminescent material. Similarly, targeted gases other than oxygen may be measured based on the luminescent film and gaseous sensitivity.

Figure 5:
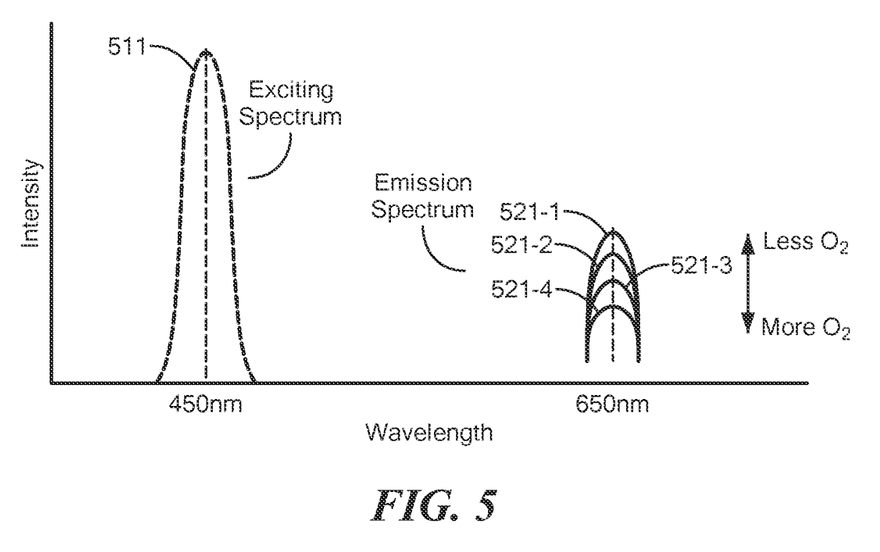
FIG. 5 is a graph of the light wavelengths emitted in the diagram of FIG. 4.

FIG. 5 is a graph of the light wavelengths emitted in the diagram of FIG. 4. Referring to FIGS. 3-5, the logic 130 is configured to compare the received red light 121 to a quenching effect of an oxygen concentration, such that the quenching effect increases with the oxygen concentration to indicate the partial pressure of oxygen in the diffused gases 124, and thus the oxygen levels in the blood and tissue underlying the patch 102. The light source 210 emits a blue light having an intensity 511, and the resulting excitation results in a red light remission having, for example an intensity of 521-1 when lower oxygen ($PtcO_2$), and increasing oxygen levels result in the red light intensity decreasing to levels of 521-2, 521-3, and to 521-4 as the increased oxygen quenches the red light response.

Figure 6:
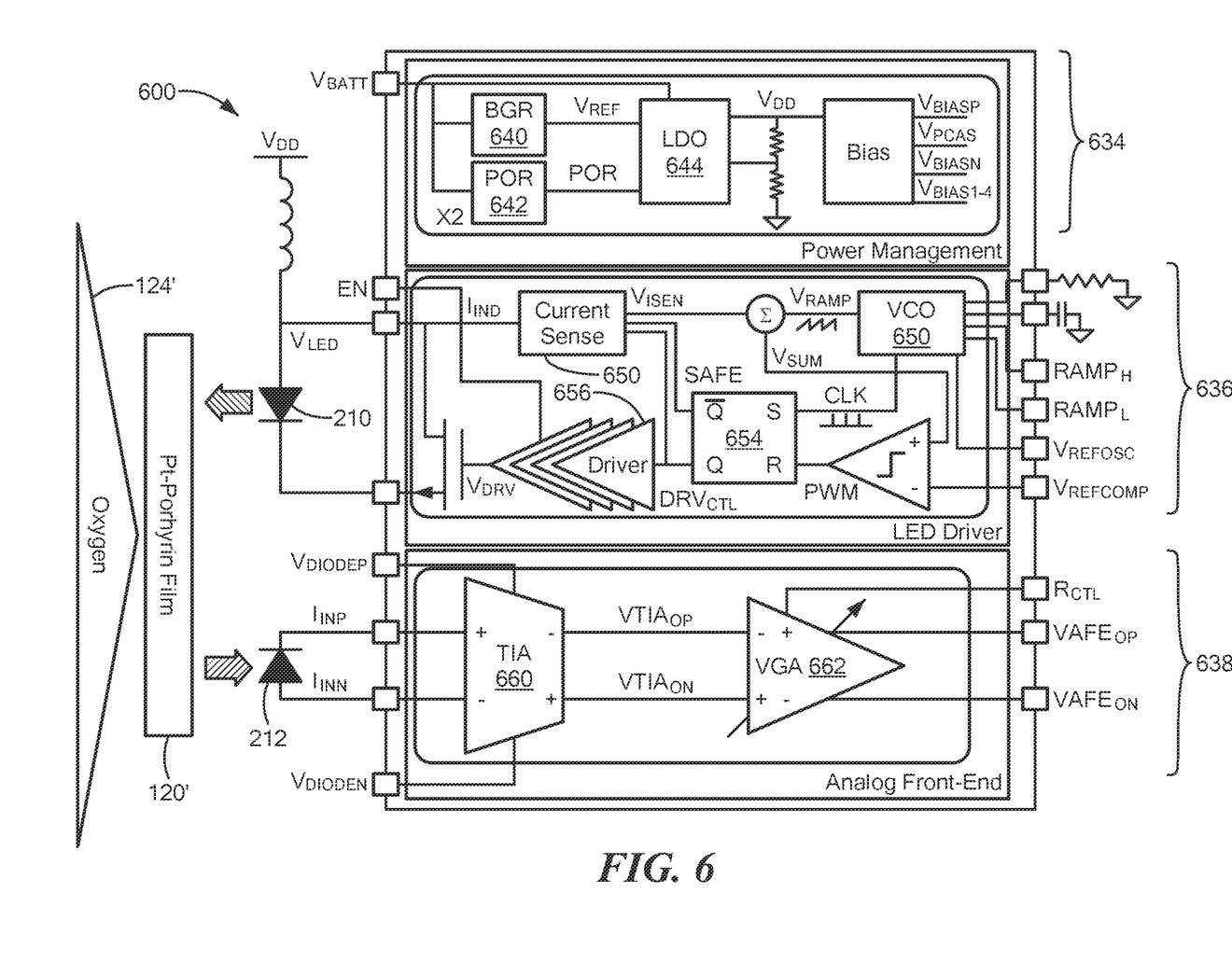
FIG. 6 is a block diagram of the wearable patch as described in FIGS. 3-5.

FIG. 6 is a block diagram of the wearable patch 102 as described in FIGS. 1-5, and FIGS. 7A-7D depict circuit schematics and graphs of the device 100. Referring to FIGS. 1-6 and 7A-7D, the circuit includes a power management portion 634 corresponding to the power supply 134, an LED driver 636 for powering and pulsing the blue LED 210, and an analog front end (AFE) 638 for receiving and generating a signal from the photodetector 212 corresponding to the remitted red light intensity indicative of the oxygen level. The logic 130 includes a mapping of luminescent diminution for an increasing oxygen availability, defined by a partial pressure of oxygen, that indicates the transcutaneous oxygen 124' diffusing through the dermal (skin) surface 126. The quenching ability resulting from increasing oxygen 124' causes the luminescent diminution, or intensity reduction, of the received red light 121 by the photodetector 212.

The power management portion 634 may be implemented as a Power Management Integrated Circuit (PMIC) including two bandgap references (BGR) 640, two power-on-reset (POR) blocks 642, two biasing circuits, and two low-dropout (LDO) regulators 644, powered off of an external 3 V battery. The BGR 640 includes 5 V CMOS devices to withstand a wide range of battery voltages (VBATT) and generates a stable reference voltage (VREF) of 1.2 V for the LDO, which converts the battery voltage to a stable 1.8 V supply voltage (VDD). A resistive feedback network sets the relationship between VREF and VDD. When the battery voltage drops below a certain level, the POR circuit provides a power-on reset signal for the LDO. The purpose of two LDO channels is to isolate the power path between the AFE and the LED driver and to distribute the load.

For example, the LED driver 136 excites the blue LED 210 with a peak wavelength of 450 nm, which excites the Pt-porphyrin film. The film emits red light of 650 nm, the intensity and lifetime of which are inversely proportional to the concentration of $O_2$. The current flowing through the photodetector 212 is proportional to the intensity of the red light from the film. Examples herein include Pt-porphyrin film having a sensitivity and responsiveness at the disclosed wavelengths. Alternate luminescent materials may of course be employed, such as rubidium based materials, and the wavelength values adjusted accordingly.

Figure 7A:
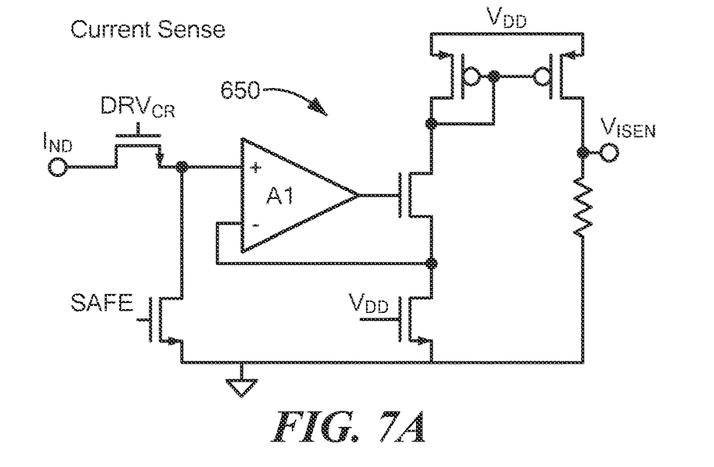
FIGS. 7A-7D show graphs of voltage and light pulses in the circuit of FIG. 6.
Figure 7B:
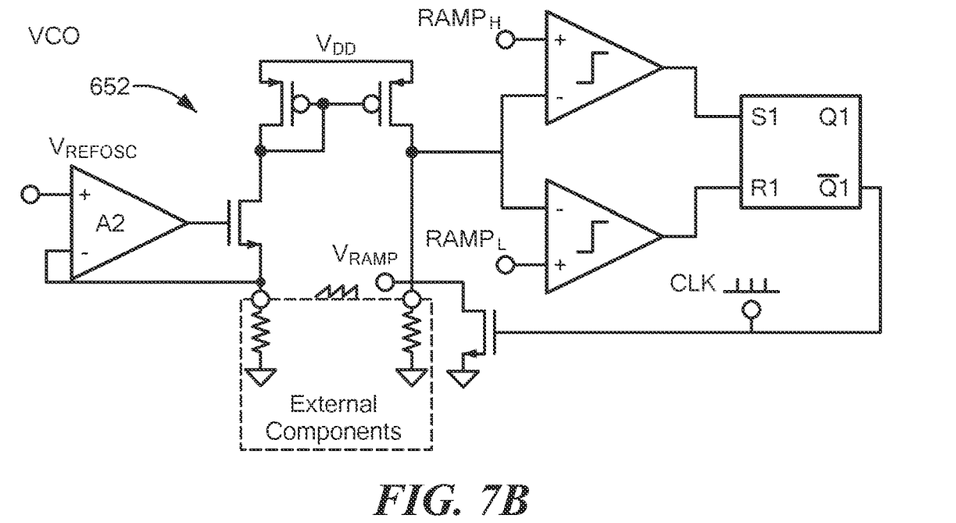
Figure 7C:
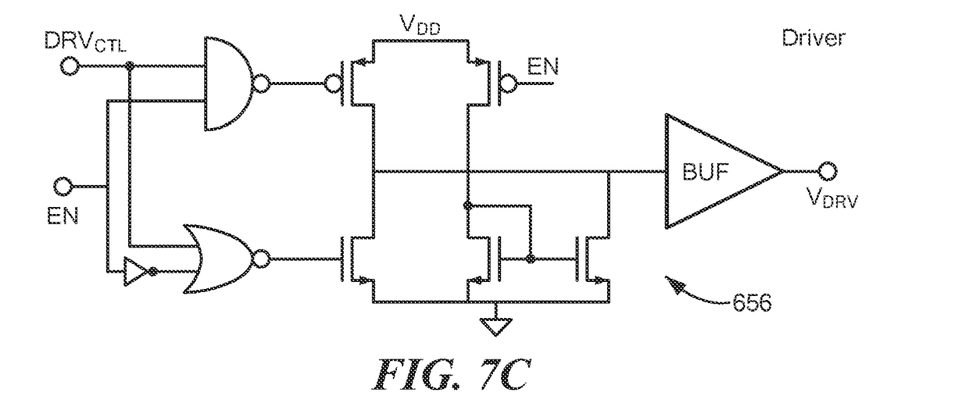
Figure 7D:
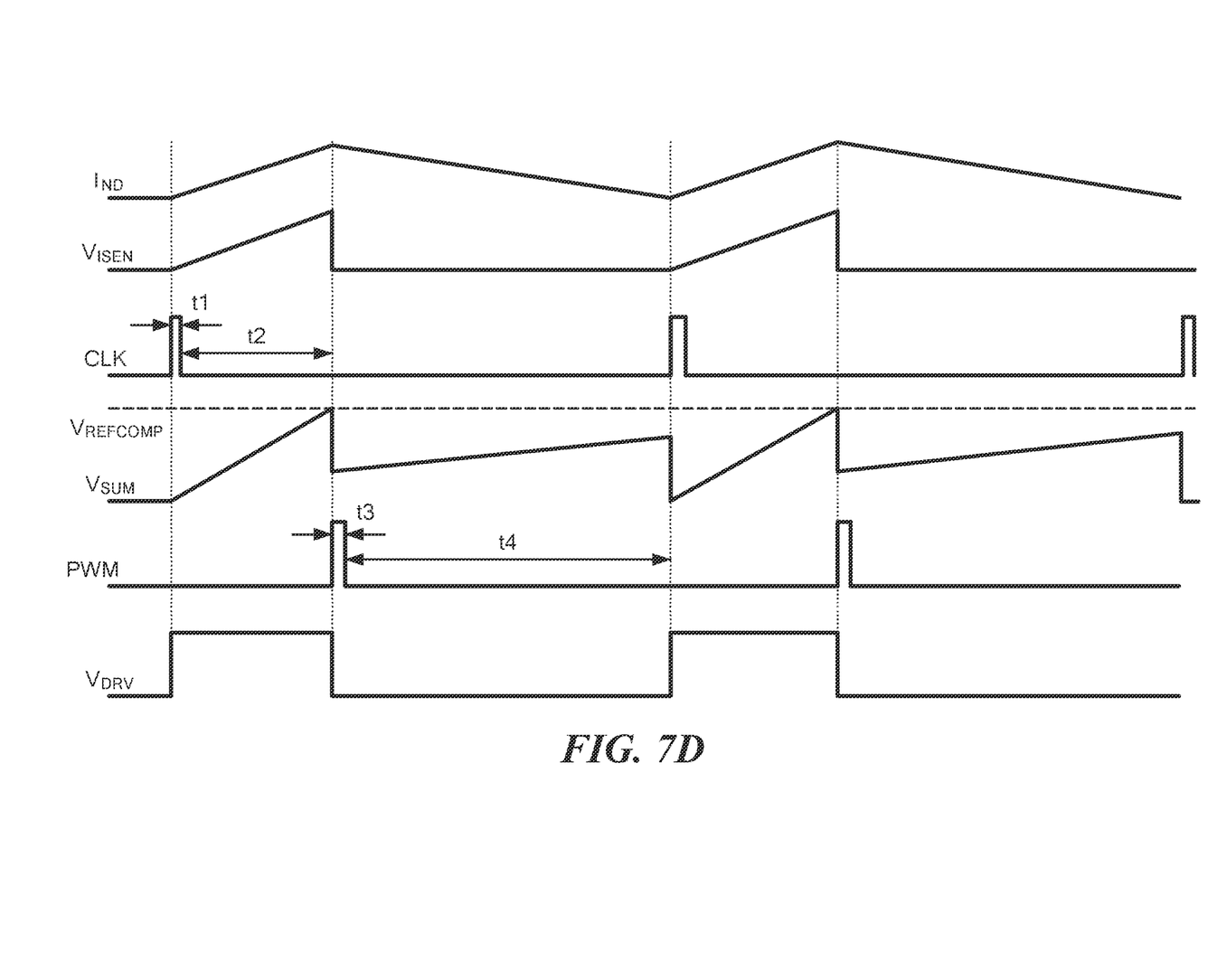

The LED driver 636 provides sufficient power to excite the blue LED with the proper intensity. It includes a current sensing block 650, a voltage-controlled oscillator (VCO) 652, a summer circuit, a comparator, an SR latch 654, and a driver 656, shown schematically in FIG. 7C. An off-chip inductor is employed to boost VDD to turn on the LED. The current sense block (FIG. 7A) measures the current (IIND) flowing through the inductor and outputs a signal (VISEN), which is then summed with the ramp signal (VRAMP) from the VCO, shown schematically in FIG. 7B, and compared with the current reference voltage VREFCOMP. This signal sets the limit of the maximum current in the inductor and keeps the driver stable. The timing diagram of the LED driver is illustrated in FIG. 7D.

The VCO generates the clock signal (CLK) and the ramp signal. VRAMP is summed with VISEN to create VSUM, which is then compared to an externally controlled reference voltage (VREFCOMP) in order to set the PWM signal. This signal resets the SR latch 654 and determines the pulse width of the DRVCTL signal. When EN is low, the driver is powered down, regardless of the DRVCTL. When enabled (EN=HIGH), VDRV controls the NMOS device based on the pulse-width modulated DRVCTL, and adjusts the current flowing through the LED. The EN signal is pulsed to reduce the power consumption of the readout. When EN is high, the LED driver pulls 16 mA current with VREFCOMP at 600 mV (increasing VREFCOMP increases IIND). When EN is low, the quiescent current of the LED driver 656, dominated by the current consumption of the VCO, is 180 mA. The externally controlled signals RAMPH, RAMPL, and VREFOSC, set the upper limit, the lower limit, and the frequency of the ramp waveform, respectively. Pulsation patterns of the blue light may vary, and are typically a series of rapid pulses interspersed between longer null intervals, as the oxygen diffusion has an inertial variance that can be effectively monitored periodically over 1-10 seconds to avoid excessive power drain.

Figure 8A:
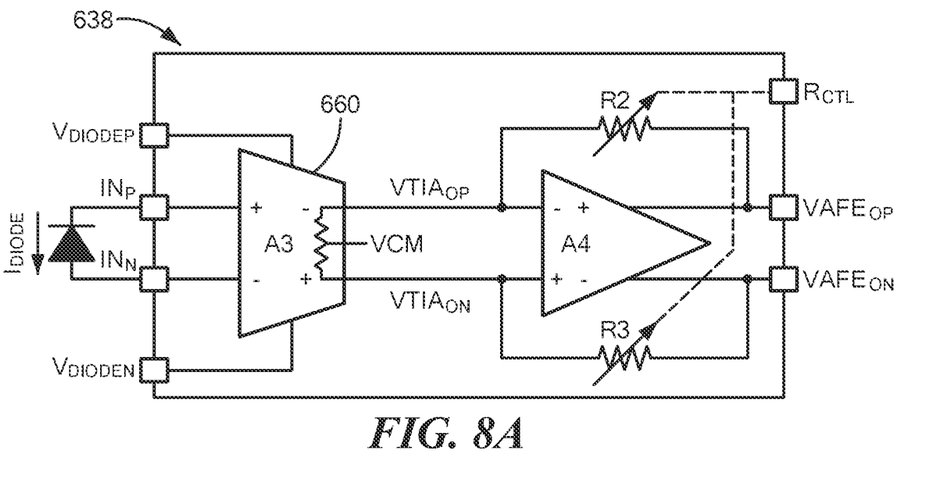
FIGS. 8A-8C shows a further detail of the analog front end of FIG. 6.
Figure 8B:
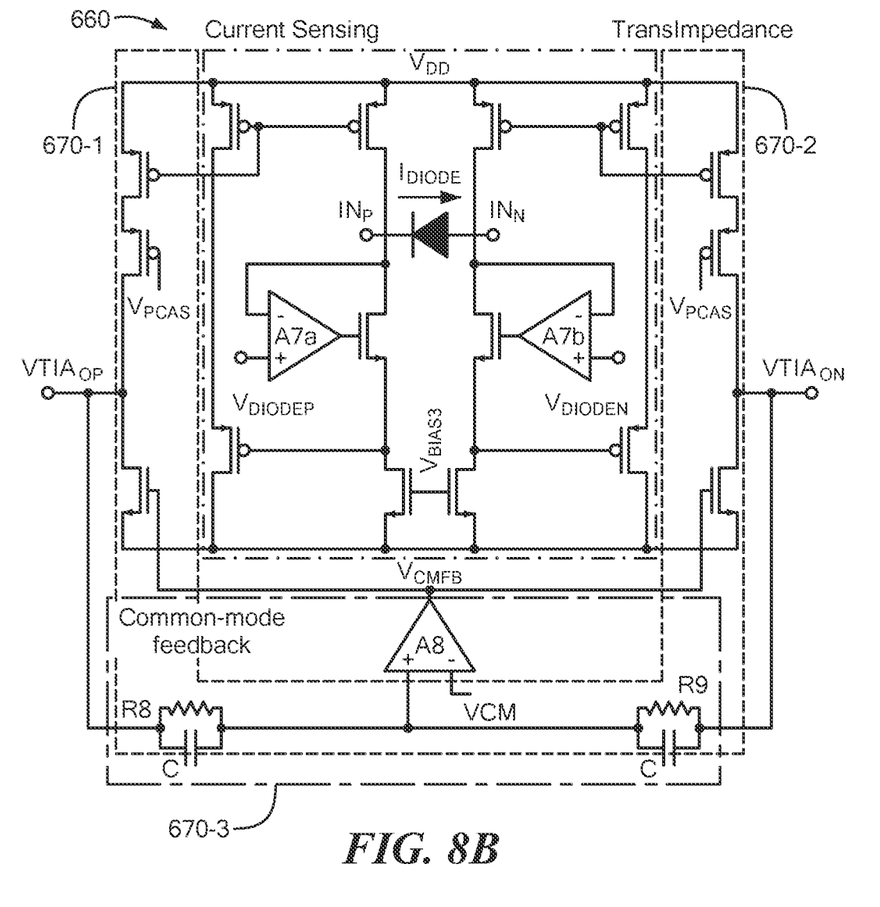
Figure 8C:
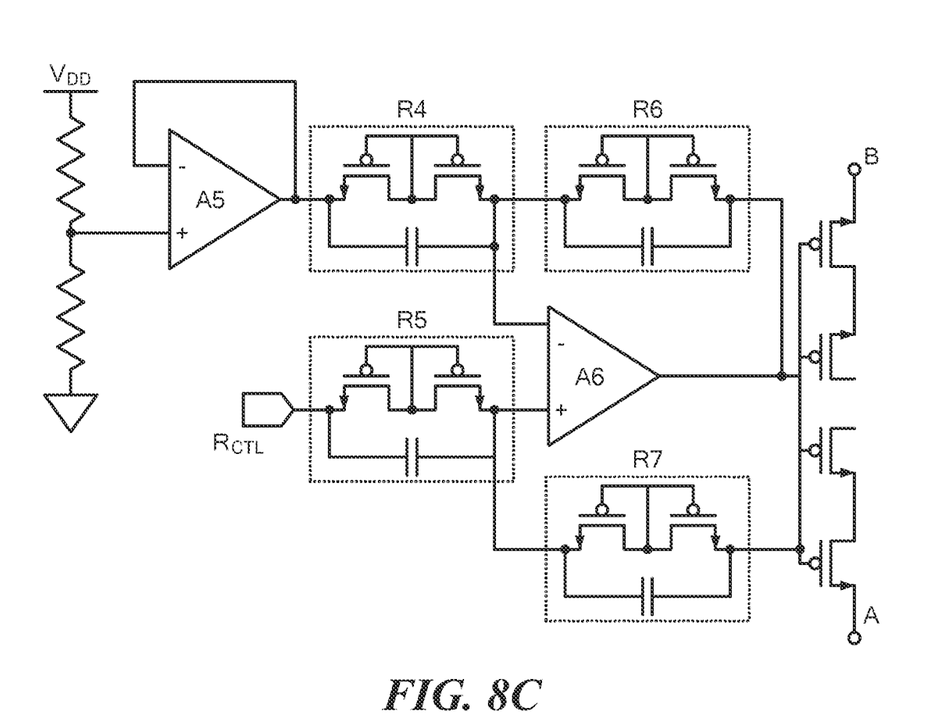

FIGS. 8A-8C shows a further detail of the analog front end 638 of FIG. 6. Referring to FIGS. 6-8C, in a particular arrangement, the AFE 638 includes two stages: a transimpedance amplifier (TIA) 660 and a variable gain amplifier 662 (VGA) 662. A differential TIA architecture minimizes the input impedance of the amplifier 662, which allows for small duty cycles and reduces common-mode noise. The cathode and the anode of the photodetector 212 connect to INP and INN inputs of the TIA 660, respectively.

The pulsing frequency of the system is based on the input impedance of the TIA and the capacitance of the photodetector 212. The TIA 660 may include current sensing 670-1, transimpedance 670-2, and common mode stages 670-3. The main purpose of the current-sensing stage 670-1 is to reduce the input impedance of the TIA with inner feedback loops created with amplifiers Ala and Alb and supplying a stable DC bias to the PD. The transimpedance stage 670-2 is designed to convert the current generated by the photodetector 212 to voltage with a gain of substantially around 50.1 kΩ using the feedback resistors R8 and R9 (shared with the common-mode feedback amplifier). The tunable gain is provided by the fully differential VGA 662, which follows the TIA. The variable gain is achieved by using pseudo resistors R2 and R3 controlled externally by RCTL.

FIG. 8C shows the schematic of the variable pseudoresistors. The design consists of a two-stage NMOS op-amp with indirect feedback compensation A5, a single-stage differential amplifier A6, and non-tunable pseudo-resistors, R4, R5, R6 and R7. Varying the control voltage RCTL changes the resistance value of tunable pseudo-resistors from a few hundred kΩ to several hundred Gο.

The intervals of light and the wavelengths thereof are depicted above in an example arrangement. Other intensities, pulsing cycles, and wavelengths may be provided and/or varied to produce the described results, possibly with alternate granularity and precision. The logic 130 in the example circuits my be provided by any suitable logic circuit, integrated circuit and/or programmed set of instructions, executed by a processor and/or embodied in a hardware or software rendering in volatile or non-volatile memory.

Figure 9:
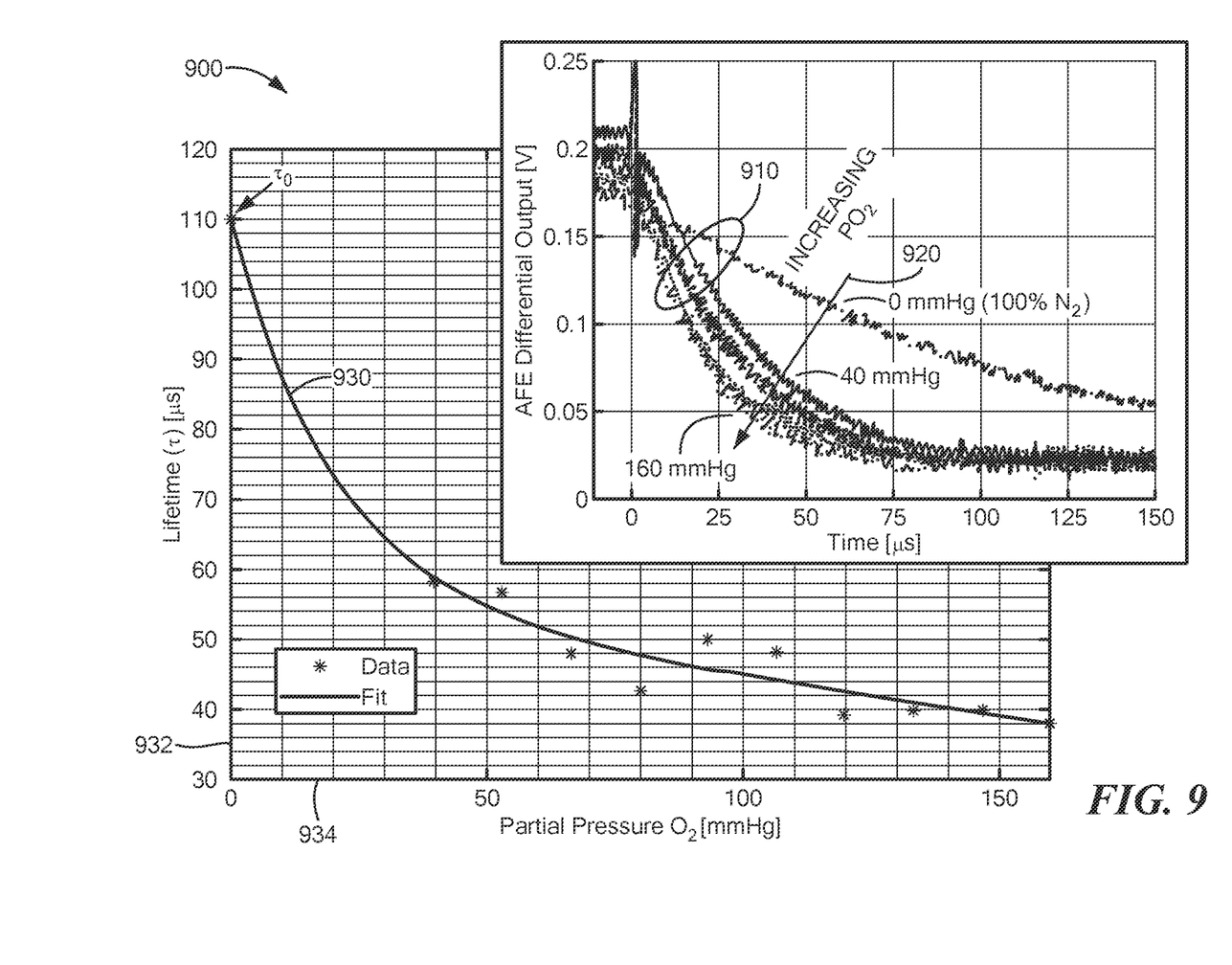
FIG. 9 shows a relation between intensity and lifetime (duration) of remitted light.

FIG. 9 shows a relation between intensity and duration of remitted light. Referring to FIG. 9, and using oxygen as an example as shown herein, a graph 900 shows measured emitted light output for various $O_2$ concentrations 910 in the environment. As the partial pressure of oxygen increases (arrow 920), the output decreases generally faster, with variations on pressure. A resulting curve 930 approximates data points as the lifetime (duration) 932 of the emitted fluorescent lifetime decreases as partial pressure of oxygen ($PO_2$) 934 increases, as per a Stern-Volmer response. In other words, the quenching effect of oxygen reduces both the intensity (strength) and lifetime (duration) that the emitted red light is detected. The relation of intensity to duration allows measurement of either or both towards computing the $PO_2$, however measurement of lifetime tends to be more robust, as described above.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A gas measurement device, comprising:
   an optical source configured to emit a series of bursts;
   a light sensitive medium including a sensing film adapted for adherence to an epidermal surface and responsive to gaseous diffusion from the epidermal surface, the light sensitive medium emits a photoluminescent response, from an oxygen based decay following each burst from the optical source, the emitted light based on a gaseous diffusion through the light sensitive medium;
   a receptor disposed for receiving the emitted light, the optical source adjacent to the light sensitive medium and between the receptor and the light sensitive medium; and
   a circuit including logic coupled to the receptor for computing a quantity of the gaseous diffusion based on the emitted light.

2. The device of claim 1 further comprising a collection medium adapted to engage a surface for coupling the light sensitive medium to a source of the gaseous diffusion, the collection medium directing diffused gases from the surface to the light sensitive medium.

3. The device of claim 2 wherein the collection medium is a planar epidermal patch adapted for receiving the gaseous diffusion.

4. The device of claim 1 wherein the light sensitive medium is responsive to the diffusion source for emitting a red light inversely proportional with a partial pressure of oxygen in the gaseous diffusion.

5. The device of claim 1, wherein the sensing film includes an oxygen sensitive luminophore for exhibiting an emission of red light based on a partial pressure of oxygen diffused through at least a portion of the sensing film.

6. The device of claim 5 wherein the sensing film is a thin film of a luminescent material.

7. The device of claim 5 wherein the sensing film is a thin film including at least one of platinum porphyrin (Pt-porphyrin) or rubidium.

8. The device of claim 4, wherein the logic is configured to compare the received red light to a quenching effect of an oxygen concentration, the quenching effect increasing with the oxygen concentration.

9. The device of claim 8 wherein the logic includes a mapping of luminescent diminution for an increasing oxygen availability, defined by a partial pressure of oxygen, that indicates the transcutaneous oxygen diffusing through the dermal (skin) surface.

10. The method of claim 1 further comprising a readout and digitizing circuit coupled to the receptor, the logic further coupled to the digitizing circuit for receiving an intensity and duration of the emitted light.

* * * * *